(12) United States Patent
Wood et al.

(10) Patent No.: US 8,524,209 B2
(45) Date of Patent: *Sep. 3, 2013

(54) COMPOSITION FOR THE PERMANENT SHAPING OF HUMAN HAIR

(75) Inventors: Jonathan Wood, Weinheim (DE); Britta Punsch, Kesseldorf (DE); Jörg Schneider, Griesheim (DE); Kornelia Weiβbach, Bad Soden (DE)

(73) Assignee: KAO Germany GmbH, Darmstadt (DE)

( * ) Notice: Subject to any disclaimer, the term of this patent is extended or adjusted under 35 U.S.C. 154(b) by 489 days.

This patent is subject to a terminal disclaimer.

(21) Appl. No.: 12/145,142

(22) Filed: Jun. 24, 2008

(65) Prior Publication Data

US 2009/0004129 A1    Jan. 1, 2009

(30) Foreign Application Priority Data

Jun. 26, 2007   (EP) .................................. 07012455

(51) Int. Cl.
  *A61K 8/81*       (2006.01)
  *A61K 8/64*       (2006.01)

(52) U.S. Cl.
  USPC ...................... 424/70.5; 424/70.15

(58) Field of Classification Search
  None
  See application file for complete search history.

(56) References Cited

U.S. PATENT DOCUMENTS

| | | | |
|---|---|---|---|
| 4,529,586 A | 7/1985 | Marco et al. |
| 4,547,365 A | 10/1985 | Kubo et al. |
| 4,673,568 A | 6/1987 | Grollier et al. |
| 5,208,014 A | 5/1993 | Dubief et al. |
| 5,293,885 A | 3/1994 | Darkwa et al. |
| 5,332,570 A | 7/1994 | Bergstrom et al. |
| 5,441,729 A | 8/1995 | Salce et al. |
| 5,520,909 A | 5/1996 | Salce et al. |
| 5,565,192 A | 10/1996 | Leroy et al. |
| 6,080,788 A | 6/2000 | Sole |
| 6,136,859 A | 10/2000 | Henriksen |
| 6,180,662 B1 | 1/2001 | Lanzendorfer et al. |
| 6,290,942 B1 | 9/2001 | Nakazato et al. |
| 6,376,455 B1 | 4/2002 | Friedli et al. |
| 6,378,530 B1 | 4/2002 | Rezvani et al. |
| 6,692,731 B2 | 2/2004 | Rose et al. |
| 6,855,312 B1 | 2/2005 | Craig et al. |
| 7,169,385 B2 | 1/2007 | Fantuzzi et al. |
| 2001/0008631 A1 | 7/2001 | Ellis et al. |
| 2001/0028887 A1 | 10/2001 | Douin et al. |
| 2004/0237218 A1 | 12/2004 | Marsh et al. |
| 2007/0141005 A1 * | 6/2007 | Wood et al. ................. 424/70.2 |
| 2008/0279803 A1 | 11/2008 | Kainz et al. |

FOREIGN PATENT DOCUMENTS

| | | |
|---|---|---|
| DE | 19926177 A1 | 12/2001 |
| DE | 10360688 A1 | 7/2005 |
| EP | 0712623 A | 5/1996 |
| EP | 1059077 | 12/2000 |
| EP | 1059081 A2 | 12/2000 |
| EP | 1391194 | 2/2004 |
| EP | 1598047 A1 | 11/2005 |
| EP | 1797861 A | 6/2007 |
| GB | 2157168 A | 10/1985 |
| WO | 8907435 A2 | 8/1989 |
| WO | 2005115315 A1 | 12/2005 |
| WO | 2006056361 A | 6/2006 |
| WO | WO 2006/056361 * | 6/2006 |

OTHER PUBLICATIONS

"Luviquat Polymer Grades," Technical Information published by BASF, 2005, pp. 1-32.*
CAS Registry No. RN 68131-40-8, Copyright 2010 ACS on STN.
Isomer: Structural Isomers—Inforplease.com; Structural Isomers; http://www.infoplease.com/ce6/sci/A0858924.html. pp. 1 and 2 (2007).
Principles of Polymer Science and Technology in Cosmetics and Personal Care; editied by E. Desmond Goddard, et al., p. 299 (1999).
Dow Corning(R) 2-8177 Emulsion; Dow Corning Corporation; Material Safety Data Sheet; pp. 1-8; Version 1.3 (2009).
Dow Corning 949 Cationic Emulsion; INCI Name: Amodimethicone and cetrimonium chloride and trideceth-12; pp. 1-3.
Product Information; Information About Dow Corning 2-8194 Microemulsion.

* cited by examiner

*Primary Examiner* — Brian Gulledge
(74) *Attorney, Agent, or Firm* — Norris McLaughlin & Marcus, P.A.

(57) ABSTRACT

The present invention concerns a composition for the permanent shaping of human hair comprising a copolymer of vinylpyrrolidone and quaternized vinylimidazole at a concentration in the range of 0.1 to 2.5% by weight calculated to total composition and process for permanent shaping human hair with the said compositions.

12 Claims, No Drawings

COMPOSITION FOR THE PERMANENT SHAPING OF HUMAN HAIR

The present invention concerns a composition for the permanent shaping of human hair used both for the permanent waving of human hair with an excellent waving effect as well as for the straightening of either naturally or chemically curled hair.

It is generally known that permanent waving is carried out in two steps, the reductive splitting of the cysteine disulfide bonds in the hair by a reducing agent, and the subsequent neutralization by application of an oxidizing agent, whereby the cysteine disulfide bonds are restored.

The reducing agent still most frequently used today is thioglycolic acid, also in form of the salts thereof, in particular its ammonium salt, although numerous other thio compounds have been proposed for this purpose, which, however, mostly did not succeed.

The compositions containing thioglycollates are customarily applied at a pH-value between 7 and 10, in particular 8.5 and 9.5.

Such compositions vary in their waving and/or straightening performance and, therefore, there is still need for further improvement.

The present invention starts from the task of providing a composition for the permanent shaping of human hair with excellent waving and straightening performance. Hair waved or straightened with composition disclosed herein looks and feels natural upon touching by hand. For waved hair it is especially important that the hair has excellent elasticity and bounce Accordingly, the first object of the present invention is a composition for permanent shaping and/or straightening hair based on at least one reducing agent at a concentration of above 2% by weight, calculated to the total composition, which further comprises copolymer of vinylpyrrolidone and quaternized vinylimidazole at a concentration in the range of 0.1 to 2.5% by weight, calculated to total composition.

Use of cationic polymers in permanent shaping compositions of keratin fibres is generally known in the art. The cationic polymers suggested until now is especially Polyquaternium-6 which is a homopolymer of dimethyl diallyl ammonium chloride. It has not been known a permanent shaping composition comprising a copolymer of vinylpyrrolidone and quaternized vinylimidazole.

Composition of the present invention comprises copolymer of vinylpyrrolidone and quaternized vinylimidazole at a concentration of 0.1 to 2.5%, preferably 0.2 to 2%, more preferably 0.25 to 1.5 and most preferably 0.25 to 1% by weight calculated to total composition.

Copolymers of vinylpyrrolidone and quaternized vinylimidazole are known with their CTFA name Polyquaternium-16, which is the most preferred copolymer of vinylpyrrolidone and quaternized vinylimidazole within the meaning of the present invention. There are various types of Polyquaternium-16 available varying with their cationic charge density, i.e. number of charge per gram polymer expressed as meq/g. According to present invention charge density is calculated at pH7.0. Within the meaning of the present invention, preferred copolymers of vinylpyrrolidone and quaternized vinylimidazole has a charge density at least 2 meq/g, preferably 3.0 meq/g, more preferably 6.1 meq/g at pH 7.0. Such polymers are available under the trade name Luviquat from BASF.

The permanent shaping compositions according to the invention comprise at least one reducing compound at a concentration of at least 2.0% by weight calculated to total composition. Preferred are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycollate, 1,2-propyleneglycol monothioglycollate (see also WO-A 93/1791), 1-3-propanediol monothioglycollate or the isomer mixture resulting therefrom, 1,3-butanediol and 1,4-butanediol monothioglycollate and the isomer mixtures therefrom, polyethylene glycol, such as di-, tri- and tetraethyleneglycol monothioglycollates, glycerol monothiolactate and further thio acids and the esters thereof, as well as mixtures thereof.

The use of inorganic reducing sulfur compounds such as sodium hydrogen sulfite is basically also possible.

The total reduction agent content in the compositions according to the invention customarily amounts from 2.0 to 15%, preferably 2.5 to 12.5% by weight, calculated to total composition as free thioglycolic acid as reference substance.

The permanent shaping compositions containing reducing agents can, if necessary, comprise alkalizing agents. Their quantity is dependent on the reducing agent and the desired pH-value of the composition. Reducing agent compositions preferably contain 0.1% to 5%, in particular 0.5% to 2.5% by weight thereof, calculated to the total composition. Alkalizing agents preferred within the scope of the invention are ammonium carbamate, ammonia and/or ammonium(bi)carbonate, and triethanolamine. It is desirable to adjust the pH-value between about 6.5 and 10.5, preferably about 7 to 9.5.

The permanent shaping compositions according to the invention are suited for use both for the permanent waving, i.e. curling of human hair and for the straightening, i.e. smoothing thereof.

The viscosity best suited for the permanent shaping compositions according to the invention proved to be in the range of 500 to 10,000 mPa·s, preferably about 1,000 to about 5,000 mPa·s, measured at 20° C. in a Brookfield viscosimeter (no. 5 spindle), whereas the viscosity suited for the straightening compositions is preferably higher in a range up to 50,000 mPa·s, preferably up to 30,000 mPa·s measured at 20° C. in a Brookfield viscosimeter (no. 5 spindle).

The viscosity is adjusted by addition of the appropriate amounts of thickening agents known per se, such as cellulose derivatives. Thickening may as well be realized by formulating a composition in form of an emulsion with the use of $C_{10}$-$C_{22}$-fatty alcohols, in admixture with long mono alkyl chain quaternary ammonium surfactants.

The permanent shaping compositions according to the present invention preferably comprise surfactants selected from anionic, nonionic, cationic and amphoteric ones. Their proportion ranges from 0.05% to 10%, in particular from 0.1% to 5% by weight, calculated to total composition.

Suitable anionic surfactants are especially the known alkyl ether sulfates and carboxylic acids, in particular in form of their alkali salts, as well as protein fatty acid condensates.

Suitable nonionic surfactants, which are preferred within the scope of the invention, are in particular $C_8$-$C_{18}$-fatty alcohol polyglycol ethers, fatty acid polyglycol esters, fatty acid alkanolamides, amineoxides, and especially $C_8$-$C_{18}$-alkyl polyglucosides.

Also possible is the incorporation of amphoteric surfactants, such as the known alkyl betaines, alkyl amido betaines, and alkyl amphoacetates.

Further according to a further preferred embodiment, permanent shaping compositions comprise at least one cationic surfactant according to general formula

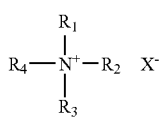

where $R_1$ s a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_2$ is a hydrogen, saturated or unsaturated, branched or non-branched alkyl chain with 1-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_3$ and $R_4$ are independent from each other H or lower alkyl chain with 1 to 4 carbon atoms, and X is chloride, bromide or methosulfate.

Concentration of cationic surfactant is in the range from 0.05% to 5%, preferably 0.1% to 2.5% by weight, calculated to total composition.

Suitable long-chain quaternary ammonium compounds which can be used alone or in admixture are in particular cetyl trimethyl ammonium chloride, dimethyl dicetyl ammonium chloride, trimethyl cetyl ammonium bromide chloride, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris-(oligooxyethyl) alkyl ammonium phosphate, cetyl pyridinium chloride, etc.

Further permanent chaping compositions of the present invention may comprise additional cationic polymer. Basically suitable are all cationic polymers listed under the generic name "Polyquaternium" in the CTFA International Cosmetic Ingredient Dictionary. Examples are Polyquaternium 6, Polyquaternium 7, Polyquaternium 10, Polyquaternium 11, Polyquaternium 22 and Polyquaternium 28, and Polyquaternium 39.

The cationic polymers also include the quaternized products of graft polymers from organopolysiloxanes and polyethyl oxazolines described in EP-A 524 612 and EP-A 640 643. Such polymer is known with its CTFA name Polysilicone-9.

Concentration of one or more additional cationic polymers is in the range from 0.05% to 2.5%, preferably 0.1% to 1.5% by weight, calculated to total composition.

Permanent shaping compositions of present invention can comprise additionally at least one organic solvent. Suitable organic solvents are 2-methyl-1,3-propanediol, mono and dialcohols or the ethers thereof, in particular mono-$C_1$-$C_3$-alkyl ether, ethanol, n-propanol, isopropyl alcohol, 1-methoxypropanol, 1-ethoxypropanol and ethoxydiglycol, diols and their esters 1,3- and 1,4-butanediol, diethyleneglycol and the monomethyl and monoethyl ether thereof, dipropylene glycol and the monomethyl and monoethyl ether thereof, glycerol, hexanetriol, ethyl carbitol, benzyl alcohol, benzyloxy ethanol, propylene carbonate, N-alkyl pyrrolidone, and urea or their mixture preferably in an amount from about 0.1% to 10% by weight, calculated to the total composition.

Permanent shaping composition of the present invention can comprise further ceramide type of compound such as cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of C10 to C22 may be incorporated into the compositions of the present invention at a concentration of preferably 0.01 to 2.5% by weight calculated to total composition.

Another preferred compound in the permanent shaping composition of the present invention is silicone compounds and especially aminated silicones such as amodimethicone available from for example Dow Corning under the brand names Dow Corning 949 Emulsion and Dow Corning 2-8194. Concentration of silicones, especially amodimethicone, is in the range of 0.05 to 2.5%, preferably 0.1 to 1% by weight calculated to total composition.

Additionally, one or more natural oil component may be incorporated into the compositions of the present invention. Suitable are such as olive oil, almond oil, avocado oil, wheatgerm oil, ricinus oil or their mixture. Concentration of these natural oil ingredients should be 0.01 to 2.5%, preferably 0.01. to 1%, more preferably 0.05 to 0.5% by weight, calculated to total composition.

Further additional compounds may be present in the permanent shaping compositions of the present invention is ubichinone of the formula

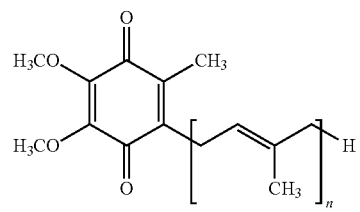

where n is a number between 1 and 10. Preferred ubichinones are the ones where n is a number between 6 and 10 and especially preferred is Ubichinone 50 where n is 10, also known as Coenzyme Q10. Concentration ubichinone of the above formula in permanent shaping compositions of the present invention is from 0.0001 to 1%, preferably from 0.0002 to 0.75%, more preferably from 0.0002 to 0.5% and most preferably from 0.0005 to 0.5% by weight, calculated to total composition.

The compositions used according to the invention can naturally comprise all the substances customarily found in permanent shaping compositions, a list of which will not be given here, and are preferably present as solutions, gels with a higher or lower viscosity, emulsions or creams. They can be single-phase products or compositions packed into separate packaging which are united upon application, as they are disclosed, for example, in DE-C 43 04 828.

In order to avoid repetition, reference is here made to the state of the art as it is described, for example, in "Ullmann's Encyclopedia of Industrial Chemistry", Vol. A12 (1986), pages 588 to 591, and in particular to the monography of K. Schrader, "Grundlagen und Rezepturen der Kosmetika", 2 nd. Ed. (1989, Hüthig Buchverlag) pages 823 to 840, as well as the article by D. Hollenberg et. al. in "Seifen-Öle-Fette-Wachse", 117 (1991), pages 81 to 87.

Composition of the present invention is used in a process for permanent waving wherein hair is washed or shampooed first and wound on the curlers, subsequently a reducing agent composition comprising at least one reducing agent at a concentration of above 2% by weight calculated to total composition and a copolymer of vinylpyrrolidone and quaternized vinylimidazole at a concentration in the range of 0.1 to 2.5% by weight, calculated to total composition is applied onto hair and after 1 to 45 min, preferably 1 to 30 min of processing time, depending on the hair strength, rinsed off from hair with tap water and an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off and curlers removed from hair. In cases where additional conditioning composition is required this may as well be applied after finishing the process as described above.

In another process as described above the curlers are removed after rinsing off the reducing agent and before applying the oxidizing agent.

Further in another process, after rinsing off the reducing agent from hair, an intermediate treatment composition is applied onto hair and without rinsing off but after removing the excess amount of intermediate treatment with a towel, oxidizing composition is applied and at the end of the processing they are rinsed off from hair and curlers are removed from hair.

It has further been found out that the use of copolymer of vinylpyrrolidone and quaternized vinylimidazole at a concentration in the range of 0.1 to 2.5% by weight, calculated to total composition, in the intermediate treatment composition improves the permanent shaping of hair as well in terms of curl appearance and natural look and feel of hair. Therefore, in another preferred form of the present invention, permanent shaping of hair is carried our with a process wherein hair is washed or shampooed first and subsequently a reducing agent comprising composition is applied onto hair and after 1 to 45 min, preferably 1 to 30 min of processing time, depending on the hair strength, rinsed off from hair with tap water and an intermediate treatment composition comprising copolymer of vinylpyrrolidone and quaternized vinylimidazole at a concentration in the range of 0.1 to 2.5% by weight, calculated to total composition is applied and without rinsing off an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off. In cases where additional conditioning composition is required this may as well be applied after finishing the above process. In case of permanent waving hair in the above process curlers are put onto hair before application of reducing composition and taken off from hair before application of oxidizing composition or after application and processing of the oxidizing composition.

The intermediate treatment composition has a pH value between 2.5 to 6, preferably 3 to 5.5 and most preferably 3 to 5.

A straightening process may also be carried out in a different process wherein hair is washed and/or shampooed and dried and reducing composition comprising at least one reducing compound at a concentration of above 2% by weight, calculated to the total composition and copolymer of vinylpyrrolidone and quaternized vinylimidazole at a concentration in the range of 0.1 to 2.5% by weight, calculated to total composition is applied onto dry hair and processed for 5 to 60 min, preferably 5 to 45 min and rinsed off with water and dried and the dry hair physically straighten with hot iron at a temperature of 130 to 210° C. and subsequently an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off.

The following examples are to illustrate the invention, but not to limit it.

EXAMPLE 1

| Alkaline Permanent Wave for Normal Hair | |
|---|---|
| Ammonium thioglycolate (60%) | 21.3 (% by wt. |
| Ammonium hydrogen carbonate | 5.0 |
| 1,3-butylene gylcol | 3.0 |
| Polyquaternium-16* | 0.5 |
| PEG-40-Hydrogenated castor oil | 0.7 |
| Perfume | 0.4 |
| Ammonia, 25% | ad pH 8.3 |
| Water | ad 100.0 |

*Luviquat ® Excellence available from BASF, which is a copolymer of vinylpyrrolidone (present at 5% by weight of the total copolymer) and quaternized vinylimidazole (present at 95% by weight of the total copolymer) having a molecular weight (by light scattering) of 40,000 and a charge density of 6.1 meq/g at pH 7.

With this composition the hair was permanently waved for about 15 minutes, rinsed and neutralized for about 8 minutes with a customary 2.5% $H_2O_2$ composition. Homogeneous wave appearance was obtained. Exclusion of Polyquaternium-16 resulted in less homogeneous perm appearance.

EXAMPLE 2

| Alkaline Permanent Wave for Normal Hair | |
|---|---|
| Ammonium thioglycolate (60%) | 20 (% by wt. |
| Ammonium hydrogen carbonate | 4.0 |
| 1,3-butylene gylcol | 3.0 |
| Polyquaternium-16* | 0.25 |
| PEG-40-Hydrogenated castor oil | 0.7 |
| Perfume | 0.4 |
| Ammonia, 25% | ad pH 8.3 |
| Water | ad 100.0 |

*Luviquat HM 552 available from BASF

With this composition the hair was permanently waved for about 15 minutes, rinsed and neutralized for about 8 minutes with a customary 2.5% $H_2O_2$ composition. Homogeneous wave appearance was obtained. Exclusion of Polyquaternium-16 resulted in less homogeneous perm appearance.

EXAMPLE 3

| Alkaline Permanent Wave for Damaged Hair | |
|---|---|
| Ammonium thioglycollate (60%) | 15.0 (% by wt.) |
| Ammonium hydrogen carbonate | 2.5 |
| Ceteth-20 | 0.7 |
| Cetrimonium chloride | 0.1 |
| 1,3-butylene gylcol | 0.5 |
| Polyquaternium-16* | 0.8 |
| Perfume | 0.4 |
| Ammonia, 25% | ad pH 8.0 |
| Water | ad 100.0 |

*Luviquat Excellence available from BASF

The permanent wave achieved with this composition was similar to the one obtained with the composition according to Example 1.

Exclusion of the Polyquaternium-16 led to waves with substantially weaker contours.

EXAMPLE 3

| Alkaline Permanent Wave for Damaged Hair | |
|---|---|
| Ammonium thioglycollate (60%) | 0.9 (% by wt.) |
| Cystein hydrochloride | 5.7 |
| Ammonium hydrogen carbonate | 1.5 |
| Acetylcystein | 0.7 |
| Cetrimonium chloride | 0.1 |
| 1,3-butylene gylcol | 0.5 |
| Polyquaternium-16* | 1.5 |
| Amodimethicone | 0.2 |
| Coenzyme Q10 | 0.05 |
| Oleic acid | 0.05 |
| Perfume | 0.4 |
| Ammonia, 25% | ad pH 9.8 |
| Water | ad 100.0 |

*Luviquat Excellence available from BASF

The permanent wave achieved with this composition was similar to the one obtained with the composition according to Example 1.

Exclusion of the Polyquaternium-16 led to substantially weaker waves.

EXAMPLE 4

Neutral Permanent Wave for Normal Hair

A permanent waving product consisting of two Compositions A and B, filled into a two-chamber packaging the chambers of which were kept separate until application, was prepared by destruction of the separating wall and applied onto human hair rolled onto curlers. The hair was rinsed after about fifteen minutes processing and neutralized for about five minutes with a 2.5% $H_2O_2$ neutralizer composition, rinsed again, shampooed and dried.

An expressive, even, intensive permanent wave was obtained.

An identical treatment which had no Polyqauternium-16 showed a visibly inferior wave.

Composition A:

| Ammonium hydrogen carbonate | 4.5 (g) |
|---|---|
| Polyquaternium-16* | 1.0 |
| PEG-65-Hydrogenated castor oil | 0.8 |
| Isopropyl alcohol | 1.5 |
| Ethoxydiglycol | 2.0 |
| Cocoamidopropyl betaine | 1.0 |
| Perfume | 0.3 |
| Coenzyme Q10 | 0.05 |
| Turbidifying agent | 0.5 |
| Ammonia, 25% | ad pH 8.4 |
| Water | ad 72.0 |

*Luviquat Excellence available from BASF

Composition B:

| Ammonium thioglycollate, 70% | 18.0 (g) |
|---|---|
| Thiolactic acid | 2.0 |
| 2-Methyl-1.3-propanediol | 0.5 |
| Ammonia, 25% | ad pH 5.5 |
| Water | ad 28.0 |

After admixture of both Compositions a ready-to-use product with a pH-value of 7.4 was obtained.

EXAMPLE 5

Neutral Permanent Wave for Dyed Hair

A permanent waving product filled into a two-chamber package was prepared in analogy to Example 4:

Composition A:

| Ammonium hydrogen carbonate | 3.5 (g) |
|---|---|
| Polyquaternium-16* | 0.5 |
| Ethanol | 0.5 |
| 1-Methoxypropanol | 1.0 |
| Cocoamidopropyl betaine | 1.0 |
| PEG-25-glyceryl cocoate | 0.8 |
| Coenzyme Q10 | 0.1 |
| Oleic acid | 0.05 |
| Perfume | 0.3 |
| Turbidifying agent | 0.5 |
| Ammonia, 25% | ad pH 8.3 |
| Water | ad 72.0 |

*Luviquat Excellence available from BASF

Composition B:

| Ammonium thioglycollate, 70% | 13.0 (g) |
|---|---|
| Thiolactic acid | 0.5 |
| 2-Methyl-1.3-propanediol | 1.5 |
| Ammonia, 25% | ad pH 5.5 |
| Water | ad 28.0 |

A product with a pH-value of 7.4 was obtained by admixture of the Compositions immediately prior to application. After application onto dyed hair as described in Example 3, this mixture resulted in an expressive permanent wave, which had not effect whatever on the color gloss and color intensity.

EXAMPLE 6

| Alkaline Permanent Waving Gel | |
|---|---|
| Ammonium thioglycollate, 70% | 15.0 (g) |
| Ammonium hydrogen carbonate | 4.5 |
| PEG-40-Hydrogenated castor oil | 0.7 |
| $C_{12}$-$C_{18}$-Fatty alcohol mixture | 3.5 |
| Cetrimonium chloride | 2.0 |
| Amodimethicone | 0.05 |
| 2-Methyl-1.3-propanediol | 0.5 |
| Polyquaternium-16* | 0.4 |
| Coenzyme Q10 | 0.1 |
| Perfume | 0.3 |
| Ammonia, 25% | ad pH 8.0 |
| Water | ad 100.0 |

| Intermediate treatment composition | |
|---|---|
| Asparagic acid | 0.25% by weight |
| Glutamic acid | 0.50 |
| Alanin DL | 0.25 |
| Magnesium sulfate | 10.00 |
| Polyquaternium-16* | 0.2 |
| Water | q.s. to 100 |

*Luviquat Excellence available from BASF

The above composition had a pH of 4.10.

EXAMPLE 7

| Straightening Composition | |
|---|---|
| Thioglycolic acid | 8.0 (% by wt.) |
| $C_{16}$-$C_{22}$-Fatty alcohol mixture | 3.5 |
| Oleth-50 | 2.5 |
| Laureth-23 | 1.5 |
| Polyquaternium-16 | 0.8 |
| Ethanol | 5.0 |
| Perfume | 0.6 |
| Monoethanolamine | ad pH 9.3 |
| Water | ad 100.0 |

*Luviquat Excellence available from BASF

This composition constitutes an effecting smoothing composition for kinky hair.

The invention claimed is:

1. Composition for the curling of human hair, comprising at least one reducing agent at a concentration of above 2% by weight, calculated to total composition, and a copolymer of vinylpyrrolidone, present at 5% by weight of the total copolymer, and quaternized vinylimidazole, present at 95% by weight of the total copolymer, at a concentration in the range of 0.1 to 2.5% by weight calculated to total composition, wherein the copolymer has a cationic charge density of at least 6.1 meq/g at pH 7.0 and a molecular weight, by light scattering method, of 40,000.

2. Composition according to claim 1, wherein the reducing agents are selected from thioglycolic acid, thiolactic acid and its salts, cystein and its hydrochloride salt and acetylcystein.

3. Composition according to claim 1, wherein it has a Brookfield viscosity of 500 to 10,000 mPa·s at 20° C.

4. Composition according to claim 1, further comprising at least one surfactant selected from anionic, nonionic and amphoteric ones at a concentration of 0.05 to 10% by weight, calculated to total composition.

5. Composition according to claim 1, further comprising at least one organic solvent at a concentration of 0.1 to 10% by weight, calculated to total composition.

6. Composition according to claim 1, further comprising at least one ubichinone of the formula

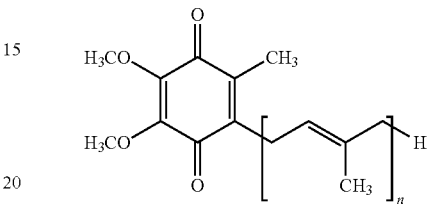

where n is a number between 1 and 10.

7. Composition according to claim 1, further comprising aminated silicone at a concentration of 0.05 to 2.5% by weight, calculated to total composition.

8. Composition according to claim 1, wherein it has a pH in the range of 6.5 to 10.5.

9. Composition according to claim 1, further comprising at least one cationic surfactant.

10. Process for permanent waving of hair, comprising the steps of, in order:
washing or shampooing hair first and then winding the hair on curlers and
applying on to the hair the composition according to claim 1 onto the hair,
at the end of the 1 to 45 min of processing time, rinsing off the composition from the hair with tap water,
applying onto the hair an oxidizing composition comprising at least one oxidizing agent, at a concentration of 0.5 to 10% by weight calculated to total of oxidizing composition,
leaving the oxidizing composition on the hair 1 to 20 min
rinsing off the oxidizing composition from the hair and removing the curlers from the hair.

11. Process according to claim 10 wherein after rinsing off the composition according to claim 1 from the hair, an intermediate treatment composition optionally comprising a copolymer of vinylpyrrolidone and quaternized vinylimidazole at a concentration in the range of 0.1 to 2.5% by weight calculated to total composition is applied onto hair and without rinsing off and after removal of the excess amount with towel, the oxidizing composition is applied and at the end of the processing they are rinsed off from hair.

12. Process for straightening hair wherein hair is washed and/or shampooed and dried and reducing composition according to claim 1 is applied onto dry hair and processed for 5 to 60 min and rinsed off with water and dried and the dry hair physically straighten with hot iron at a temperature of 130 to 210° C. and subsequently an oxidizing composition comprising at least one oxidizing agent at a concentration of 0.5 to 10% by weight calculated to total of oxidizing composition, is applied onto hair and left on the hair 1 to 20 min and rinsed off.

* * * * *